(12) United States Patent
Huang et al.

(10) Patent No.: US 10,922,816 B2
(45) Date of Patent: Feb. 16, 2021

(54) MEDICAL IMAGE SEGMENTATION FROM RAW DATA USING A DEEP ATTENTION NEURAL NETWORK

(71) Applicant: Siemens Healthcare GmbH, Erlangen (DE)

(72) Inventors: Qiaoying Huang, Edison, NJ (US); Xiao Chen, Princeton, NJ (US); Mariappan S. Nadar, Plainsboro, NJ (US); Boris Mailhe, Plainsboro, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 51 days.

(21) Appl. No.: 16/506,123

(22) Filed: Jul. 9, 2019

(65) Prior Publication Data

US 2020/0065969 A1 Feb. 27, 2020

Related U.S. Application Data

(60) Provisional application No. 62/723,178, filed on Aug. 27, 2018.

(51) Int. Cl.
*G06T 7/11* (2017.01)
*G06T 7/00* (2017.01)
(Continued)

(52) U.S. Cl.
CPC .............. *G06T 7/11* (2017.01); *G06N 3/0454* (2013.01); *G06N 3/084* (2013.01); *G06N 20/00* (2019.01);
(Continued)

(58) Field of Classification Search
CPC ............... G06T 7/11; G06T 7/0012; G06T 2207/20081; G06T 2207/20084; G16H 50/50; G06N 20/00; G06N 3/0454; G06N 3/084; G06K 9/4609; G06K 9/6267; G06K 2209/05
See application file for complete search history.

(56) References Cited

U.S. PATENT DOCUMENTS

| | | | |
|---|---|---|---|
| 2019/0054194 A1* | 2/2019 | Yu | A61B 5/0042 |
| 2019/0266436 A1* | 8/2019 | Prakash | G06N 3/0481 |
| 2020/0211710 A1* | 7/2020 | Do | G06T 7/155 |

OTHER PUBLICATIONS

Bresch et al, "Region Segmentation in the Frequency Domain Applied to Upper Airway Real-Time Magnetic Resonance Images," 2009, IEEE Transactions on Medical Imaging, vol. 28, No. 3, pp. 323-338 (16 pages total) (Year: 2009).*

(Continued)

*Primary Examiner* — David F Dunphy

(57) ABSTRACT

Various approaches provide improved segmentation from raw data. Training samples are generated by medical imaging simulation from digital phantoms. These training samples provide raw measurements, which are used to learn to segment. The segmentation task is the focus, so image reconstruction loss is not used. Instead, an attention network is used to focus the training and trained network on segmentation. Recurrent segmentation from the raw measurements is used to refine the segmented output. These approaches may be used alone or in combination, providing for segmentation from raw measurements with less influence of noise or artifacts resulting from a focus on reconstruction.

19 Claims, 6 Drawing Sheets

(51) Int. Cl.
*G06N 3/08* (2006.01)
*G16H 50/50* (2018.01)
*G06N 3/04* (2006.01)
*G06N 20/00* (2019.01)
*G06K 9/62* (2006.01)
*G06K 9/46* (2006.01)

(52) U.S. Cl.
CPC .......... *G06T 7/0012* (2013.01); *G16H 50/50* (2018.01); *G06K 9/4609* (2013.01); *G06K 9/6267* (2013.01); *G06K 2209/05* (2013.01); *G06T 2207/20081* (2013.01); *G06T 2207/20084* (2013.01)

(56) References Cited

OTHER PUBLICATIONS

BrainWeb. "Simulated Brain Database" obtained from https://brainweb.bic.mni.mcgill.ca/brainweb/ on Jun. 25, 2019. p. 1-2.
Caballero, Jose, et al. "Application-driven MRI: Joint reconstruction and segmentation from undersampled MRI data." International Conference on Medical Image Computing and Computer-Assisted Intervention. Springer, Cham, 2014.
Liu, Fang, et al. "Fast realistic MRI simulations based on generalized multi-pool exchange tissue model." IEEE transactions on medical imaging 36.2 (2016): 527-537.
Lohit, Suhas, Kuldeep Kulkarni, and Pavan Turaga. "Direct inference on compressive measurements using convolutional neural networks." 2016 IEEE International Conference on Image Processing (ICIP). IEEE, 2016.
MRiLab. "A Numerical MRI Simulator" obtained from https://mrilab.sourceforge.net on Jun. 25, 2019. p. 1-2.
Ronneberger, Olaf, et al. "U-net: Convolutional networks for biomedical image segmentation." International Conference on Medical image computing and computer-assisted intervention. Springer, Cham, 2015.
Schlemper, Jo, et al. "A deep cascade of convolutional neural networks for MR image reconstruction." International Conference on Information Processing in Medical Imaging. Springer, Cham, 2017.
Schlemper, Jo, et al. "Cardiac MR segmentation from undersampled k-space using deep latent representation learning." International Conference on Medical Image Computing and Computer-Assisted Intervention. Springer, Cham, 2018.
Sun, Liyan, et al. "Joint CS-MRI reconstruction and segmentation with a unified deep network." International Conference on Information Processing in Medical Imaging. Springer, Cham, 2019.
Wu, Dufan, et al. "End-to-end abnormality detection in medical imaging." arXiv preprint arXiv:1711.02074 (2017).
Xingjian, S. H. I., et al. "Convolutional LSTM network: A machine learning approach for precipitation nowcasting." Advances in neural information processing systems. 2015.

* cited by examiner

MEDICAL IMAGE SEGMENTATION FROM RAW DATA USING A DEEP ATTENTION NEURAL NETWORK

RELATED APPLICATIONS

The present patent document claims the benefit of the filing date under 35 U.S.C. § 119(e) of Provisional U.S. Patent Application Ser. No. 62/723,178, filed Aug. 27, 2018, which is hereby incorporated by reference.

BACKGROUND

The present embodiments relate to segmentation of a medical image. Most image segmentation tasks start from existing images. Magnetic Resonance (MR) imaging measures in the spatial-frequency domain (the so-called k-space), and the MR images are reconstructed from the k-space data before further analysis. Similarly, Computed Tomography measures sinograms, which are reconstructed from the sinogram or projection space to the image space. The traditional pipeline of image segmentation treats reconstruction and segmentation as separate tasks. Using reconstruction prior to segmentation introduces image noise, residual artifacts, and/or potential loss of information due to imperfect reconstruction of images. Without the final segmentation quality as a target, the reconstruction algorithm may discard image features that are critical for segmentation but less influential to image quality.

Several end-to-end learning frameworks have been proposed for segmentation in various applications. In an unsupervised brain segmentation method, both reconstruction and segmentation are treated simultaneously using patch-based dictionary sparsity and a Gaussian mixture model. This method is not suitable for complicated scenarios. In another approach, two neural networks (LI-net and Syn-net) predict cardiac segmentation from under-sampled k-space data. The Syn-net uses UNet to map a zero-filling image (inverse Fourier transform of under-sampled k-space) directly to segmentation maps. The LI-net exploits latent space features and requires fully-sampled images during training. In yet another approach, a deep neural network architecture includes reconstruction and the segmentation sub-networks pretrained and fine-tuned with shared encoders. The final segmentation depends on the combination of the intermediate segmentation results. The segmentation sub-network is trained on reconstructed images, which contain artifacts and noises and may influence the performance of segmentation.

SUMMARY

By way of introduction, the preferred embodiments described below include methods, systems, and instructions in non-transitory computer readable media for segmentation from raw data. Various approaches provide improved segmentation from raw data. Training samples are generated by medical imaging simulation from digital phantoms. These training samples provide raw measurements, which are used to learn to segment. The segmentation task is the focus, so image reconstruction loss is not used. Instead, an attention network is used to focus the training and trained network on segmentation. Recurrent segmentation from the raw measurements is used to refine the segmented output. These approaches may be used alone or in combination, providing for segmentation from raw measurements with less influence of noise or artifacts resulting from a focus on reconstruction.

In a first aspect, a method is provided for segmentation from raw data of a magnetic resonance imager. The magnetic resonance imager acquires k-space data representing response from a patient. An object of the patient represented in the k-space data is segmented by a machine-learned neural network. The machine-learned neural network has a segmentation network recurrently applied to output an output segmentation of the object in response to input of the k-space data to the machine-learned neural network. An image based on the segmentation is generated.

In one embodiment, the acquisition uses undersampling according to an undersampling mask, such as for MRI fast imaging. The machine-learned neural network includes a data consistency layer configured to replace k-space lines from a reconstruction image with the k-space data for the k-space lines based on input of the undersampling mask.

In another embodiment, the machine-learned model includes a sequence of reconstruction blocks and data consistency layers. A last one of the data consistency layers outputs to the segmentation network. The segmentation is output after two or more of the recurrent applications of the segmentation network.

The machine-learned neural network was trained with a segmentation loss and not a reconstruction loss. The network, when applied for segmenting, is designed for the segmentation task despite input of the raw data. Various training data may be used. Since the input is to be raw data and the loss is based on segmentation rather than reconstruction, the training data includes raw data (i.e., pre-reconstruction measurements) and segmentation ground truth. In one approach, the difficulty in collecting samples of training data is overcome by simulation of medical imaging from digital phantoms. The simulation may include undersampling and/or fully sampled raw data output by the simulation may be undersampled.

Where the machine-learned neural network includes recurrent operation, the segmentation network may be applied any number of times, such as two or three. The segmentation loss is determined in training from the output of the recurrent application. The segmentation network used in the recurrent application may include various components, such as a regularization block and a data consistency layer being recurrently applied to generate the segmentation.

Where the machine-learned neural network includes an attention network, the attention network generates multi-class attention maps from pre-output segmentations by the segmentation network. These maps are used to focus the features on the segmentation of the various classes. Images are multiplied based on probability maps of different tissues as the pre-output segmentations. Results of the weighting are input to a regularization block of the segmentation network.

In a second aspect, a method is provided for segmentation from raw data of a magnetic resonance imager. The method is the same as for the first aspect, but the machine-learned neural network includes an attention network instead of or in addition to the recurrently applied segmentation network. Other features or embodiments of the first aspect may be used in the second aspect.

In a third aspect, a method is provided for training segmentation from raw data of a reconstruction medical imager. Training data including pre-reconstruction measures and segmentation maps is generated by medical imaging simulation of digital phantoms. A neural network is trained to segment based on the pre-construction measures as input and segmentation maps as ground truth. The trained neural network is stored.

In one embodiment, k-space or sinogram data is generated as the pre-reconstruction measures. For simulation of under-sampling, some of the k-space or sinogram data is removed. The training data resulting from the simulation of under-sampling is used in machine training. The training is with a segmentation loss and not a reconstruction loss. The segmentation maps are used as ground truth for the segmentation loss. The neural network may be defined to include recurrent segmentation and/or an attention layer configured to output multi-class segmentation probability maps to a regularization block.

The present invention is defined by the following claims, and nothing in this section should be taken as a limitation on those claims. Features or embodiments of one aspect or type of claim (e.g., method, system, or computer readable storage medium) may be used in other aspects or types of claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Segmentation from k-space, sinogram, or other pre-reconstruction measurements is machine learned with an end-to-end recurrent and/or attention network. The task of medical image segmentation commonly involves an image reconstruction step to convert acquired raw data to images before any analysis. By performing image segmentation directly from raw (e.g., k-space) data, noise, artifacts, and/or information loss from optimizing for reconstruction may be avoided.

In one embodiment, the end-to-end framework or architecture for machine learning and resulting machine-learned model includes a task-driven attention module that recurrently utilizes intermediate segmentation estimation to facilitate image-domain feature extraction from the raw data, thus closely bridging the reconstruction and the segmentation tasks. The intermediate segmentation is recurrently exploited as an anatomical prior that provides guidance to recover segmentation-driven image features from the raw data, which in turn improves segmentation performance.

Network parameters are shared by using the same segmentation network or UNet in the different iterations of the recurrence. This may assist in overcoming noisy data.

One challenge for end-to-end segmentation learning is the preparation of the training data with ground truth segmentation. Most studies simulate the raw k-space data from DICOM images using a direct Fourier transform. Realistic k-space data can rarely be recovered from the images alone due to the complex-value nature of MR and common MR post-processing practices that may alter the acquisition. In addition, it is hard to obtain the ground truth segmentation for training. Manual labeling is prone to imperfect reconstruction and human error for small anatomy structures. To address the challenge of ground truth training data in end-to-end study, labeled training data is generated for segmentation by exploiting imaging modality simulators and digital phantoms.

In different approaches, image segmentation is recurrently performed directly from under-sampled k-space data; the attention module guides the network to generate segmentation-driven image features to improve the segmentation performance; or under-sampled k-space data are generated with segmentation maps by exploiting an MRI simulator and digital brain phantoms. Each approach may be used independently from the others or in any combination of two or three of the approaches.

Figure 1:
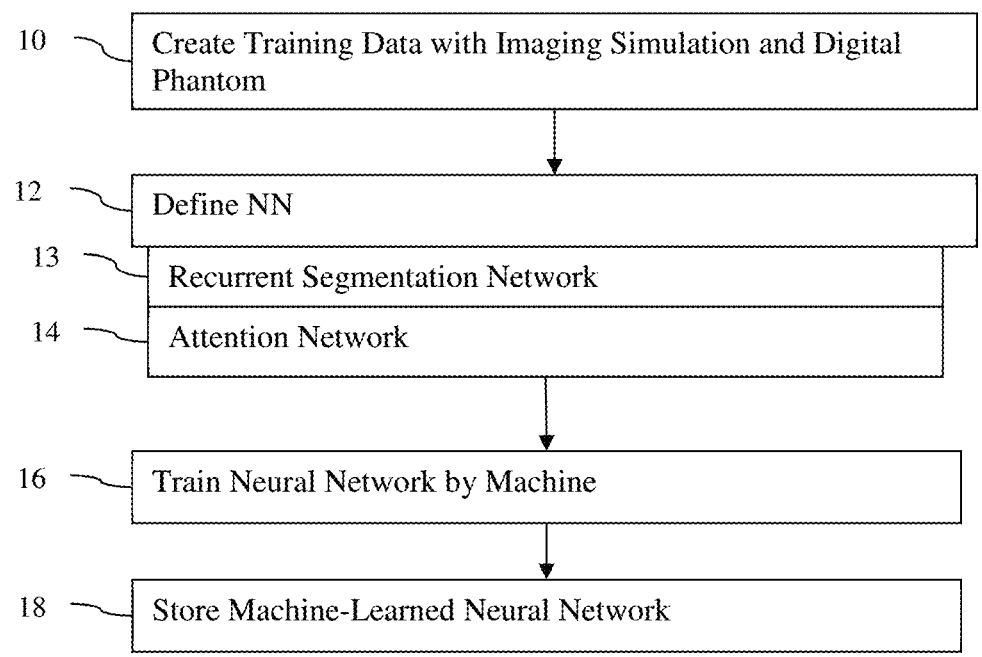
FIG. 1 is a flow chart diagram of one embodiment of a method for machine learning to segment from raw data.

FIG. 1 is a flow chart diagram of one embodiment of a method for machine training segmentation from raw data of a reconstruction medical imager. In one embodiment, simulation of medical imaging on a digital phantom generates the training data. As an additional or alternative feature, the machine learning model is defined to include segmentation recurrence (i.e., recurrent application) and/or an attention layer combining segmentation and image information. The training uses a segmentation loss without a reconstruction loss.

The method is implemented by a machine, such as a computer, workstation, server, or other processing component, with access to a database of hundreds or thousands of training data samples. The machine learns, based on a defined architecture, to segment from input pre-reconstruction (i.e., raw) data. The raw data of the samples is from scans of patients by a reconstruction-based medical imager and/or from simulation of medical imaging by the reconstruction-based medical imager on digital phantoms. The reconstruction-based medical imager is a MR, computed tomography (CT), positron emission tomography (PET), single photon emission computed tomography (SPECT), or other medical imager that reconstructs from a measurement space to an image space. The training data samples are of the measurements in the measurement space, such as sinograms for CT or k-space data for MR.

The acts are performed in the order shown (numeric or top-to-bottom), but other orders may be used. For example, act 12 may be performed prior to act 10.

Additional, fewer, or different acts may be provided. For example, acts 13 and/or 14 are not provided. In another example, acts for application of the machine-learned network are provided, such as the acts of FIG. 5.

In act 10, the machine creates training data. The training data includes a plurality or many samples of raw data from the measurement domain (i.e., pre-reconstruction measures) and corresponding segmentation maps as the ground truth. The pre-reconstruction measures are a sinogram, k-space data, projection data, or other measures that do not provide for specific three-dimensional locations per datum.

The segmentation maps are in the image domain. The segmentation maps represent a probability of a given location representing a given tissue. The probability may be binary, such as a binary map where 1 represents the location being of the tissue of interest and 0 represents the location being of other tissue. The probability may be at any resolution, such as an integer from 0-100 or any number of values in a range (e.g., 0-1 in 0.1 increments). For each sample, any number of segmentation maps may be provided. One map may have different labels for different tissue per location. Multiple maps may be provided for different tissues.

In one embodiment, four classes of tissue are to be segmented in an MRI of the brain. Four brain segmentation masks provide for four classes of tissue: 0-Background, 1-CSF, 2-Gray Matter and 3-White Matter. The brain may include other classes, such as 11 brain tissues. The CSF, Gray Matter and White Matter cover most parts of the brain. The other eight tissues, such as vessels, skull, and skin, are grouped as the background mask. This multi-class brain segmentation for MR is used as an example herein. In other embodiments, two classes (e.g., CSF and background), classes without a background or catch all, segmentations for other organs, and/or segmentations for other types of reconstruction-based medical imaging are gathered as ground truth.

The training data (e.g., raw data samples and ground truth segmentations) are generated by medical imaging simulation of digital phantoms. Realistic k-space data is generated with one or more ground truth segmentation maps per sample. The MR scanner simulator MRiLab or other simulator (e.g., JERMIS) for a reconstruction-based medical imager provides a realistic virtual MR or other scanning environment. The simulation of the imager may include scanner system imperfection, acquisition pattern and data generation and recording.

The simulation simulates scanning an object. For example, digital brain phantoms, such as the digital phantoms from BrainWeb, are used as the object "scanned" in the MRI simulator. The phantoms are representations of the object. Digital phantoms are data-based or computerized models of the object. By using digital phantoms, various variations in size, shape, tissue characteristics, tissue distribution, or other modeling parameter may be altered to create additional digital phantoms, allowing for additional samples. The alterations may span ranges of possible values for the various programmable parameters in the object model (digital phantom). Actual or physical phantoms may be used in other embodiments.

For each sample, each brain tissue type has known spatial distributions from the digital brain phantom. Accordingly, the segmentation maps for ground truth are known. Each tissue type has a unique set of values of MR physical parameters such as T1 and T2 used for the MR scan simulation. Fully-sampled k-space data is then simulated by scanning the digital brain in simulation. K-space data is generated by simulating scanning of the digital phantoms with segmentation maps defining locations of the various tissue types.

Each simulated sample (set of k-space measurements for a given scan) provides the segmentation map from the digital phantom as ground truth and k-space data from the simulated scan. By varying spatial distribution of tissue and/or other characteristics of the digital phantoms, additional samples and ground truth segmentation for machine training are generated. To mimic realistic MR scanning, white Gaussian noise may be added to the k-space data at one or more levels (e.g., different magnitude and/or distributions of noise), creating additional samples of training data.

The simulation is of a full sampling. To provide raw data representing less than a full sampling (e.g., MR fast imaging), an undersampled scan may be simulated, such as simulating based on an under-sampling mask defining a rate of undersampling and line order. Alternatively, the k-space data from the full sampling is processed, removing some of the raw data (e.g., removing k-space or sinogram data) to simulate undersampling scan. Under-sampling is performed retrospectively by keeping a subset of the full-sampled data.

Figure 4:
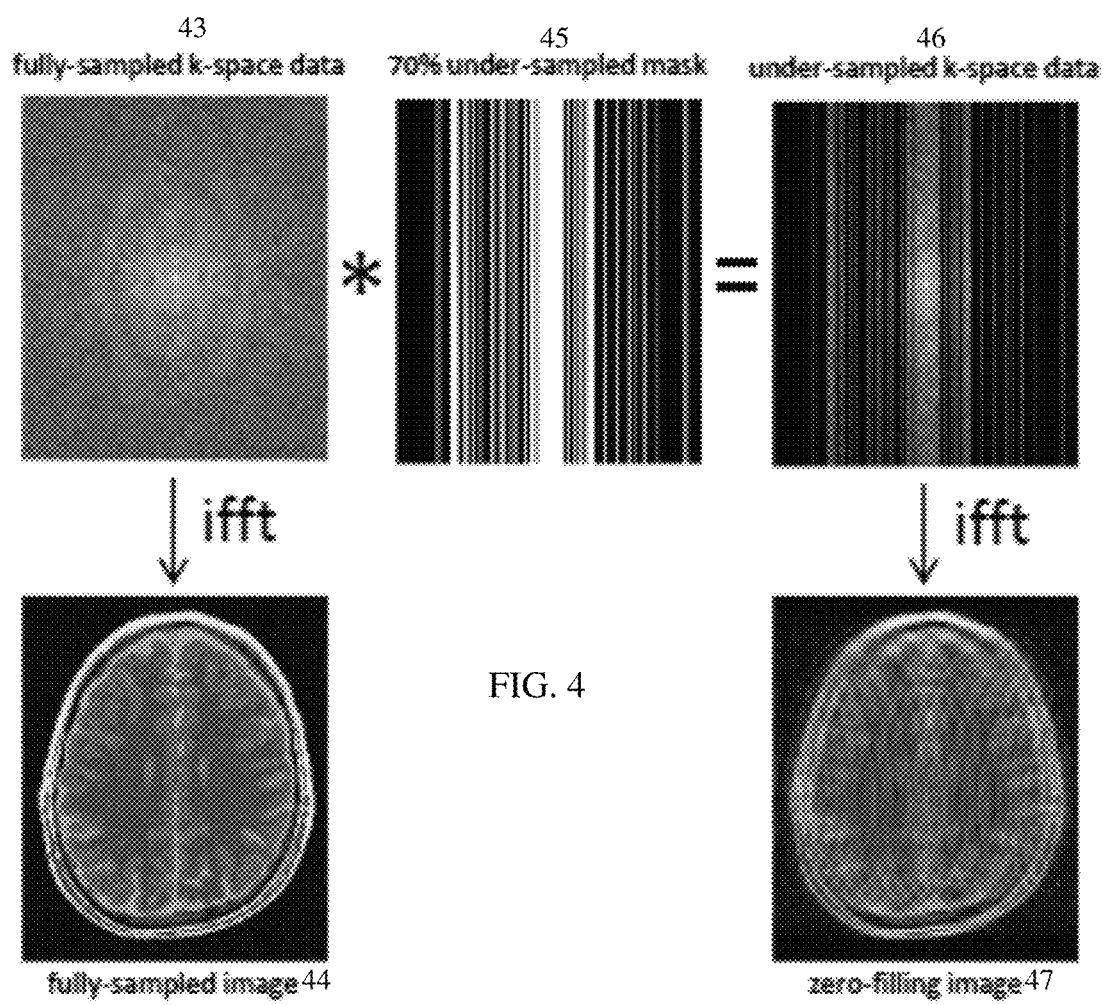
FIG. 4 illustrates an example of generation of under-sampled k-space data for use as the raw data.

FIG. 4 shows an example. Under-sampled k-space data 46 is obtained by employing an undersampling mask 45 on the fully sampled k-space data 43. A 70% sample rate is shown, but other sample rates for undersampling and/or other distribution of k-space lines may be used. Additional samples of training data may be generated from each simulation by using different undersampling masks 45. A fully-sampled image 44 (e.g., inverse fast Fourier transform of the fully-sampled k-space 43) may contain noise and compromise the segmentation performance. Similarly, a zero-filling image 47 generated from the under-sampled k-space data 46 via inverse Fourier transform may be generated.

The fully-sampled image 44 and/or zero-filling image 47 may be generated from the input k-space data 43, 46 for use in the machine learning. In one embodiment, the machine learning neural network never sees the fully-sampled data 43, instead receiving the undersampled k-space data 46. Rather than input of reconstructed images optimized for reconstruction, k-space or raw data is input. The first layer may reconstruct, but the reconstruction is to place the data into an image domain rather than including learnable parameters to optimize the reconstruction. To the extent learnable parameters are included in the inverse fast Fourier transform or other reconstruction algorithm, the optimization for segmentation loss instead of reconstruction loss trains for reconstruction directed to segmentation rather than optimal reconstruction.

In alternative or additional embodiments, the samples are from actual scans of patients. Some or all of the samples of the training data may be from scans of patients and expert manual or processor-based segmentation of images reconstructed from the scans.

In act 12 of FIG. 1, the neural network is defined. A programmer or designer defines the architecture of the network. The various blocks, connections, flow, processes, learnable parameters, and/or other characteristic of the neural network are set and/or linked to create the neural network to be trained. In other embodiments, other types of architectures than a neural network are defined.

The neural network is defined for learning to output segmentation. The locations of one or more tissues are output, in part, based on machine learning performed for the defined neural network.

Segmentation from raw data may be generally divided into two subproblems: reconstruction and segmentation. For deep learning-based reconstruction on under-sampled k-space: $x = f_{Rec}(y, m)$, where $x \in R^{2 \times w \times h}$ is the reconstructed image. For MR, the real and imaginary parts are concatenated in the first dimension in this representation. y is the under-sampled k-space data, and m is the under-sampling mask indicating the position of sampling. $f_{Rec}$ is a deep neural network to be optimized. If optimizing for a reconstruction loss, the $l_2$ loss: $l_2(x, x_{gt}) = \|x - x_{gt}\|_2$ may be used. In the case of segmentation, the reconstruction loss is not used. Instead, a segmentation loss is used.

The neural network is defined to include convolution, pooling, softmax, fully connected, ReLU, BN, long term short term memory (LSTM), and/or other layers in a cascade, dense block, UNet, or other arrangement or combinations of arrangements. Any number of input channels and output channels may be defined.

Figure 2:
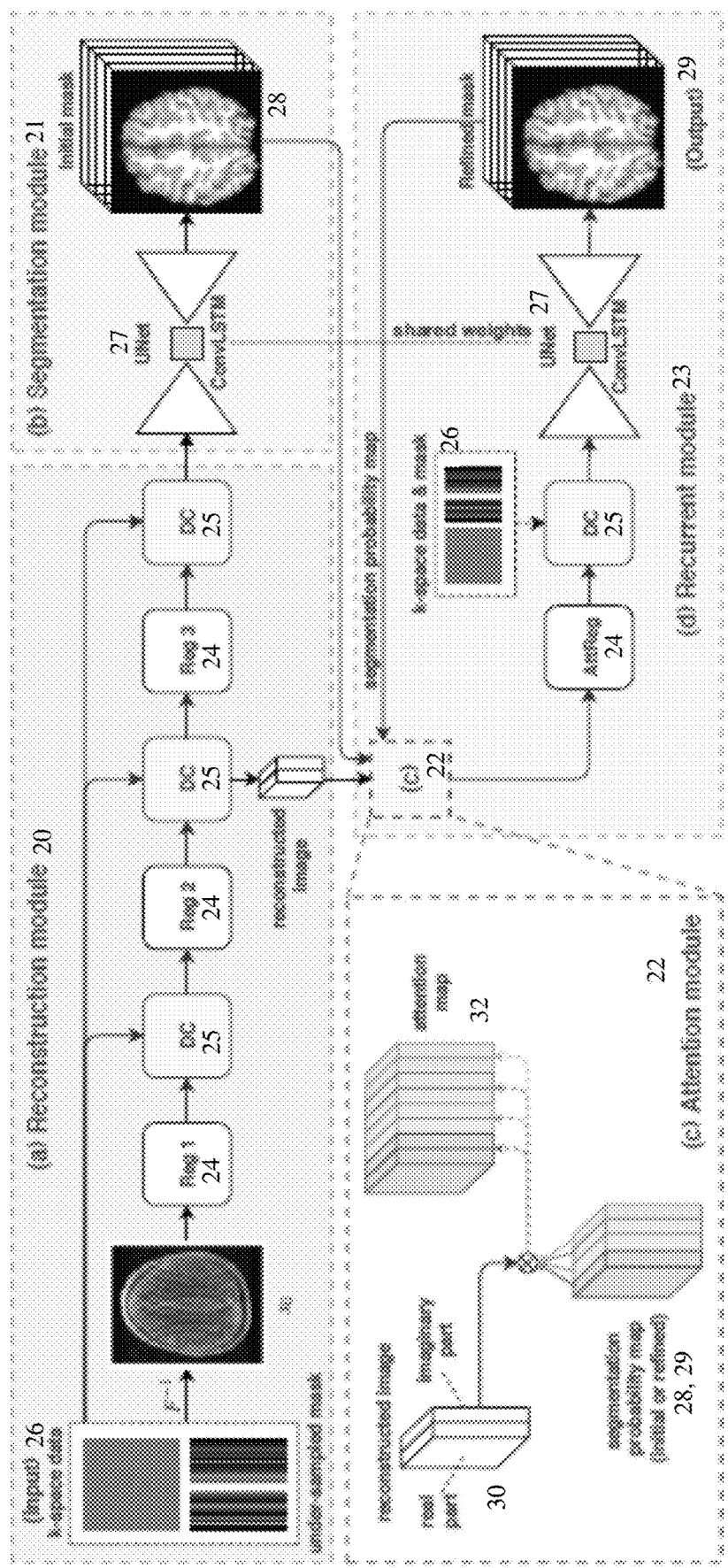
FIG. 2 illustrates one embodiment of a neural network architecture for segmentation from raw data.

In one embodiment, the neural network is defined to include recurrent segmentation network 13 and/or an attention layer or network 14. FIG. 2 shows one example of an end-to-end segmentation framework or architecture. The neural network includes a reconstruction module or network 20, a segmentation module or network 21, an attention module, network or layer 22, and a recurrent module or network 23. Additional, different, or fewer sub-networks or modules for the neural network may be defined. For example, the recurrent module 23 or network is part of the reconstruction module or network 20 and the segmentation module or network 21 is used in a recurrent (e.g., iterative or repetitive) manner.

The reconstruction network 20 includes a sequence of reconstruction blocks 24 and data consistency layers 25. Any number of reconstruction blocks 24 and/or data consistency layers 25 may be used. Deep learning-based iterative reconstruction is realized by cascading a series of reconstruction blocks 24 and data consistency layers 25. Other arrangements may be used. At last one of the data consistency layers 25 outputs to the segmentation network 21. The k-space data 26 is input to the reconstruction network 20. Where the k-space data is undersampled, the undersampling mask may also be input. The first layer or process of the reconstruction network 20 is to reconstruct from the k-space input to the image domain. Any reconstruction may be provided, such as a zero-filled inverse fast Fourier transform.

Figure 3A:
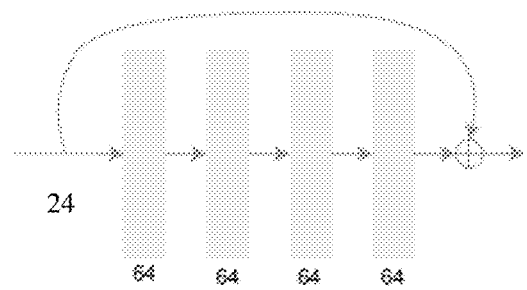
FIGS. 3A-C show example sub-networks of the neural network of FIG. 2.
Figure 3B:
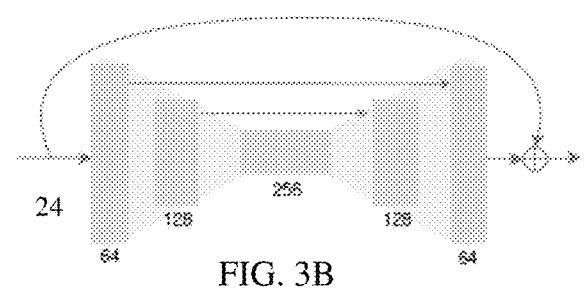

The reconstruction blocks 24 are regularization blocks. For example, a cascaded convolutional neural network (CNN) is used as the regularization block 24. FIG. 3A shows one example cascaded CNN where a sequence of four convolution layers are provided. Each layer includes 64 kernels. In one embodiment, each layer is a combination of convolution, BN and ReLU. Other numbers of layers and/or kernels may be used. The summation of the output with the input represents learning residuals as part of optimization in training. As another example, a UNet is used as the reconstruction block 24. FIG. 3B shows an example where convolutional layers are arranged with downsampling and upsampling into an encoder-decoder pair connected at a bottleneck. In the example of FIG. 3B, the number of kernels starts at 64, increasing to 256 at the bottleneck, and then decreasing back to 64 at the output. Skip connections at the same resolution are shown. In alternative embodiments, skip connections are not used, other numbers of layers are provided, and/or other numbers of kernels are used. Other regularization blocks, such as a denseNet, may be used as the reconstruction block 24.

The reconstruction blocks 24 take as input the zero-filled fast Fourier transform reconstructed image $x_0$, or the output from the DC layer $x_{dc}$, and outputs an image x. Each reconstruction block 24 has a same architecture. In alternative embodiments, different reconstruction blocks 24 have different architectures.

The data consistency layer 25 is defined or configured to maintain consistency in reconstruction with the input k-space data. Function blocks are defined in the layer to perform logic operations. The consistency may be enforced by replacement and/or constraint. The reconstructed image output by the preceding reconstruction block 24 is transformed using a fast Fourier or other transform into k-space. The differences between the k-space data from the reconstructed image and the original k-space data are used to check for and maintain data consistency. The realization and fidelity of the data may be checked and corrected. The data consistency layer 25 compensates for any difference between the estimated and the measured k-space data.

In one embodiment where undersampling is used, the data consistency layer 25 replaces k-space lines from a reconstruction image with the k-space data for the k-space lines based on input of an undersampling mask. The k-space data transformed from the reconstructed image has a full sampling. The k-space data for lines provided in the input data replace the sampling lines from the full sampling, creating a full sampling formed from some lines due to reconstruction and other lines from the input data. The undersampling mask defines the lines to be replaced. An inverse fast Fourier transform or other reconstruction is applied to the resulting full sampling k-space data, forming an image for input to the next reconstruction block 24.

The reconstructed image includes real and imaginary parts. The reconstruction blocks 24 and data consistency layers 25 use two channel input and two channel output. One input channel and one output channel are for the real part, and one input channel and one output channel are for the imaginary part. In other embodiments, the real and imaginary information are combined for one channel input or output or only the real information is used for the image.

The segmentation network 21 is a UNet 27, such as an image-to-image or encoder-decoder arrangement of convolution and/or other layers. Other architectures may be used, such as a DenseNet or cascaded fully convolutional network. Other layers or subnets may be included. For example, a reconstruction block 24 and data consistency layer 25 may be included in the segmentation network 21.

Figure 3C:
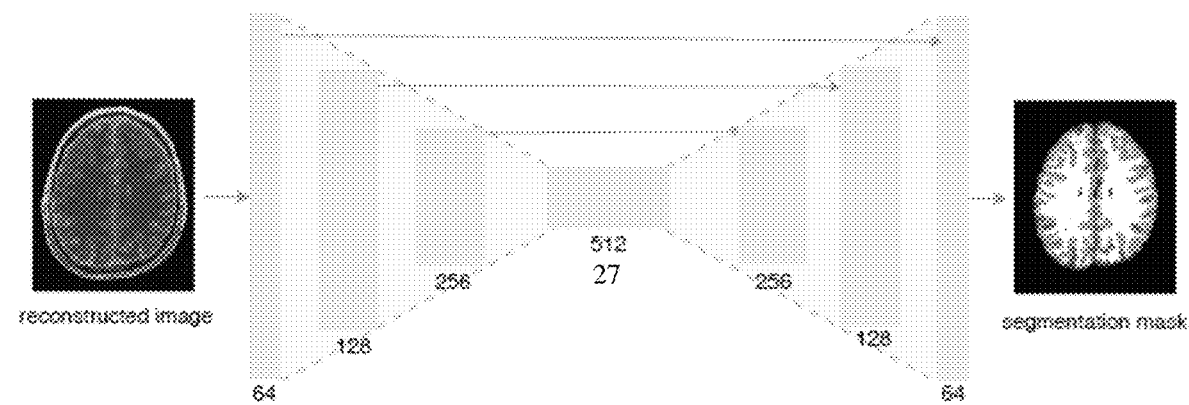

FIG. 3C shows an example UNet 27 with skip connections from the layers at the same resolution in the encoder and decoder. The encoder and decoder include three downsampling and upsampling layers with convolution at each, but more or fewer may be used. 512 features in the form of convolution kernels are provided in the bottleneck. 64, 128, and 256 features are provided at three other resolutions. Other UNet 27 architectures may be used.

The input to the UNet 27 and segmentation network 21 is a reconstructed image. An image reconstructed after the last data consistency layer 25 is input. The output is a segmentation map 28. The segmentation network 21 is to use the reconstructed image x to predict segmentation probabilities: $s=f_{seg}(X)$. $f_{seg}$ is a deep neural network (e.g., UNet 27) that may be optimized by segmentation loss. The segmentation loss, given the spatial distribution, is the cross-entropy loss: $l_{ce}(s, s_{gt})=-\Sigma_{s^i \in s} s_{gt}^i \log(s^i)$. Other losses may be used.

The output is a segmentation map 28. Multiple segmentation maps 28 may be output. For example, each location is labeled as one of four tissue classes. A single segmentation map 28 with the four labels may be output, or segmentation maps 28 for different four different classes may be output. A given location may have different probabilities of belonging to different classes, so the labels or separate maps 28 may assign probabilities to the different locations for the different classes. Any resolution of probability may be used, such as a range of 0-100 in integers or binary.

The segmentation network 21 is applied recurrently. The segmentation network 21 is applied twice or more, such as three, four, or more times. In the initial application, the segmentation network 21 outputs the segmentation maps 28 as initial segmentation maps. These initial segmentation maps are not the final outputs or final segmentation and are output for further processing by the neural network. In response to input of the k-space data with or without an undersampling mask, the neural network generates multiple iterations of the segmentation maps.

The initial and subsequent segmentation maps 28, 29 other than the final segmentation map 29 (i.e., the pre-output segmentation maps) are output to the attention network or layer 22. The attention layer 22 is defined as a logic or computer programmed operation or operations without learnable parameters. In alternative embodiments, the attention layer 22 includes one or more learnable parameters.

The attention layer 22 generates multi-class attention maps. The attention maps combine segmentation and reconstruction information to focus learning of features from the reconstruction on the segmentation. In end-to-end training, it is beneficial to share information among different tasks. The attention module bridges the gap between reconstruction and segmentation to facilitate learning segmentation-aware features in the image domain.

In the brain tissue example, the brain segmentation map or maps 28, 29 are used as anatomical priors to guide image reconstruction such that the segmentation information is explicitly utilized to extract segmentation-aware image features in deep learning from the raw k-space data. The attention network 22 facilitates the segmentation-aware learning. The attention mechanism may only consider two classes in one forward pass. In the four-class example, multi-class attention maps 32 simultaneously distinguish features among the four classes.

After one forward pass through the image reconstruction module or network 20 and the segmentation module or network 21, an initial segmentation result or map 28 is obtained. The segmentation maps, $s \in \mathbb{R}^{4 \times w \times h}$ have four tissue maps in separate channels, which are concatenated along the first dimension: $s=s^1 \oplus s^2 \oplus s^3 \oplus s^4$ where $s^i$ indicates the $i^{th}$ class prediction. Four segmentation maps 28 for the four classes are formed. The segmentation maps 28 are probability maps. After a softmax layer in the UNet 27 ensures the sum of the four different classes (probabilities) for each location is 1, the maps are utilized for attention.

To create the attention maps 32, the images 30 are weighted based on the segmentation maps 28, 29. Any weighting may be used, such as mapping weights with a look-up table to ranges of probabilities. In one embodiment, the weighting is by multiplication of the image by the segmentation maps. Each of the four segmentation probability maps 28, 29 are element-wise (i.e., location-by-location) multiplied with the input image features $x_{t-1} \in \mathbb{R}^{2 \times w \times h}$ to generate new features $x_t \in \mathbb{R}^{8 \times w \times h}$, represented by:

$$x_t = (s_{t-1}^1 \odot x_{t-1}) \oplus (s_{t-1}^2 \odot x_{t-1}) \oplus s_{t-1}^3 \odot x_{t-1}) \oplus (s_{t-1}^4 \odot x_{t-1})$$

where subscript t represents the $t^{th}$ intermediate result or recurrence. In the example of FIG. 2, the image is treated as a real image and an imaginary image. As a result, each image is multiplied by the segmentation map of each class. The two channels of images 30 and four channels of segmentation maps 28, 29 create eight channels of attention maps 32. Other numbers of attention maps 32 may be created.

The images to be multiplied are any of the reconstructed images from the reconstruction network 20 or elsewhere in the neural network. In the example shown in FIG. 2, the reconstructed image 30 to be used is the image in the image domain output from the second to last of the data consistency layers 25 or created at a beginning of the next reconstruction block 24. This same image is used for later recurrences. Alternatively, an updated reconstruction is used, such as output by the data consistency layer 25 of the recurrent network 23.

The attention maps 32 are input to the recurrent network 23. The recurrent network 23 includes a reconstruction block 24, a data consistency layer 25, and a UNet 27. Additional, different, or fewer components may be provided. For example, additional pairs of reconstruction blocks 24 and data consistency layers 25 are provided.

The reconstruction block 24 is the same or different architecture as used in the reconstruction network 20. Rather than receiving a reconstruction image from an inverse fast Fourier transform of the k-space data, the attenuation map or maps 32 are input. The new image features $x_t$ are input to the regularization block 24 for learning attention features (referred as AttReg). In one embodiment, the difference between AttReg and Reg in the reconstruction module is the input channel size: AttReg has 8 instead of 2 channels.

The data consistency layer 25 is the same check as used for data consistency in the reconstruction network 20. A different check may be used.

The UNet 27 is the same UNet used in the segmentation network 21. In other embodiments, a different instance of the same UNet 27 or a different UNet with shared features (i.e., training enforces the UNets 27 to learn and have the same features) is used in the recurrent network 23. The output of the attention-assisted image feature extraction (e.g., output from the data consistency layer 25 of the recurrent network 23) is fed to the same segmentation network 21 or UNet 27 with shared weights to generate a new segmentation estimation $s_t$. $s_t$ may be expressed as follows.

$$s_t = (f_{Seg}; f_{DC}; f_{AttReg})(x_t),$$

where $s_t$ is the new segmentation estimation. The UNet 27 outputs new segmentation maps 29. For example, four segmentation maps 29 formed by probability maps for the four different classes in the brain tissue example are generated.

Depending on the number of recurrences, the first generated segmentation maps 29 from the recurrent network (i.e., recurrence of 1-2 total iteration of segmentation) may be the final segmentation output. Where the number of recurrences is higher, then the segmentation maps 29 may be fed to the attention network 22 for another iteration in the recurrent network 23. By explicitly utilizing intermediate segmentation results for reconstruction, or more precisely image feature extraction, segmentation-driven features will be learned, which in turn improves segmentation performance during training with the back-propagation algorithm. In the example of FIG. 2, the attention layer 22, the UNet 27 as a segmentation network, the regularization block 24, and the data consistency layer 25 of the recurrent network 23 are recurrently applied to generate the final segmentation for output.

Segmentation feature learning is treated as a recurrent procedure in the defined architecture such that a final result is achieved by iterating the attention module several times. Given under-sampled k-space data y and mask m, the defined neural network is to learn to segment the brain in T iterations, where T is two or more (i.e., recurrence of one or more). An example algorithm for the neural network is given by:

Algorithm 1: SERANet: Segmentation with Recurrent Attention Network

```
input : under-sampled k-space data y, under-sampling mask m, N, T
1   x_0^(N-1), x_0^(N) ← f_Rec(y, m) ;           // initial reconstruction feature x_0
2   s_0 ← f_Seg(x_0^(N)) ;                        // initial segmentation result s_0
3   if t ≤ T then
4   |   x_t ← f_DC ○ f_AttReg(x_0^(N-1), s_{t-1}) ;   // Attention module
5   |_  s_t ← f_Seg(x_t) ;                        // Recurrent segmentation
output: s_T
``` where N is the number of $Reg_0$ blocks 24 and DC layers 25. Lines 1 and 2 generate the initial reconstructed image $x_0$ and brain tissue map $s_0$ by the reconstruction network 20 and the segmentation network 21, respectively. Then lines 3 to 5 represent a recurrent segmentation-aware reconstruction and segmentation process of the recurrent network 23 with the included attention layer or network 22. The attention module $f_{AttReg}$ takes the initial reconstruction feature $x^{N-1}$ (feature from the N−1 reconstruction block 24) and segmentation probability maps $s_{t-1}$ as input and generates new image $x_t$. To capture and memorize the spatial information at different recurrences, a ConvLSTM layer may be integrated into the UNet 27 for segmentation.

The objective function of the whole model is defined as $l_{ce}(s_T, s_{gt})$, where $s_T$ denotes the output of the final iteration. The reconstruction module does not see nor need any ground truth reconstruction image during training given the defined architecture. The recovered image content is guided by the segmentation error solely, which focuses the aim to recover image domain features from the raw data that best suits the segmentation task, rather than the conventional reconstruction task. The usage of "reconstruction" to name the module is just for conceptual simplicity.

In act 16 of FIG. 1, the machine (e.g., image processor, server, or computer) trains the neural network to segment. The machine trains the defined neural network to output a segmentation of one or more classes. The same or different machine used to create the training data is used to train. For example, one or more workstations generate the training data (e.g., simulation of medical imaging of digital phantoms to provide raw data, undersampling masks, and segmentation maps). One of the workstations or a different processor (e.g., server) trains using machine learning from the examples of the training data, which are stored in a database or other memory.

The machine learns to determine a segmentation by location based on input of pre-reconstruction data from a scan of an actual patient. Any machine learning may be used. In one embodiment, deep learning is used. Using a piecewise-differentiable function or other deep learning function, the machine trains a neural network. Other deep learned, sparse auto-encoding classifiers may be trained and applied. Support vector machine, Bayesian network, probabilistic boosting tree, sparse auto-encoding classifier, or other now known or later developed machine learning may be used. Any semi-supervised, supervised, or unsupervised learning may be used. Hierarchal, cascade, or other approaches may be used.

For deep learning for a defined neural network, the machine training is unsupervised in learning the features to use and how to classify given the learned feature vector. The network is trained with training data. Samples of input data with ground truth are used to learn. For deep learning, the classifier learns the features of the input data to extract from the training data. Alternatively, the features, at least for the input, are manually programmed, such as filtering the scan data and inputting the results of the filtering. The training relates the input data to the classification through one or more layers. One layer may relate feature values to the class. For deep-learned networks, there may be further layers creating further abstract features from outputs of pervious layers. The resulting machine-trained classifier defines inputs, convolution kernels, down-sampling, weighting, connections, and/or combinations thereof to output a classification and/or probability of class membership by spatial location.

The pre-reconstruction measures as input and segmentation maps as ground truth are used to train through optimization. The segmentation loss and not a reconstruction loss are used to train. A loss or comparison of reconstruction results to ground truth is not used in the optimization or learning. During training, the difference between a final output segmentation and the ground truth segmentation are used to adjust values of one or more learnable parameters of the neural network. The optimization solves for the values of the learnable parameters that result in the neural network, as trained, outputting segmentation maps closest to or sufficiently close to the ground truth given the corresponding input for the ground truth.

The segmentation loss may be a cross-entropy loss, but other loss functions may be used. Adam or another optimization may be used. The difference between the ground truth and the predictions by the network is minimized.

After creation, the machine-learned network includes the defined architecture with values for various parameters, such as convolution kernels, down sampling weights, weights, and/or connections. The values of the learned parameters and/or the network as trained are stored in act 18. The machine-learned network is stored in a memory, such as memory of the machine or the database with the examples. The machine-learned network may be transmitted to a different memory. The machine-learned neural network may be duplicated for application by other devices or machines, such as processors of MR scanners. The memories of MR scanners may store copies of the machine-learned network for application for specific patients.

Figure 5:
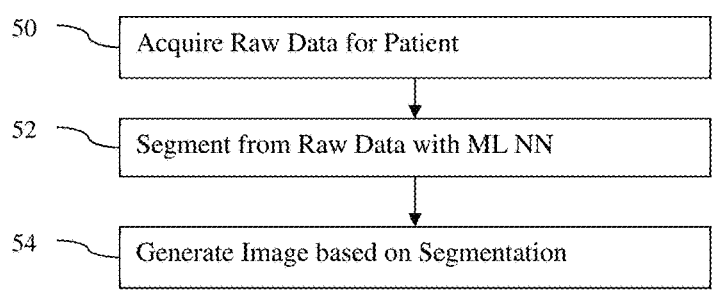
FIG. 5 is a flow chart diagram of one embodiment of a method for segmentation with a machine-learned network.

FIG. 5 is a flow chart diagram of one embodiment of a method for segmentation from raw data of a MR or other reconstruction-based imager. The stored machine-learned network is applied to segment from a scan of a patient. A scan of the patient is performed, and the k-space or other pre-reconstruction data is used to determine the spatial locations of different tissues. Segmentation is provided directly from k-space measurements or raw data prior to reconstruction.

The acts are implemented by a reconstruction-based medical imager and/or workstation. An MR, CT, PET, or SPECT scanner scans the patient. The system of FIG. 7, a server, workstation, scanner, or other machine segments from the acquired pre-reconstruction data.

Additional, different, or fewer acts may be provided. For example, the segmentation is output to a memory (e.g., computerized medical record) instead of displayed in act 54. The acts are performed in the order shown (top to bottom), but other orders may be used.

In act 50, the medical imager, such as an MR imager, acquires data representing response from the patient. A sinogram, projection, or k-space data are acquired. The acquisition is by scanning a patient and measuring response. Alternatively, the acquisition is from a memory, such as loading k-space data from a previous scan of a patient.

The acquired data may be from undersampling. For example, a fast MR scan is performed. An undersampling mask defines the k-space lines to sample and k-space lines not to sample. Alternatively, a full sampling is performed.

In act 52, an image processor, such as a controller or processor of a medical imager, segments an object of the patient represented in the k-space data. The machine-learned neural network is applied by inputting the k-space or raw data from the scan of the patient. The undersampling mask may be input as well.

The machine-learned neural network, having been trained with training data generated by undersampling, generates an output segmentation map or maps. The machine-learned neural network uses the learned values for the parameters and the architecture to generate the output segmentation. In the embodiments shown in FIG. 2, a sequence of reconstruction blocks and data consistency layers output image data in the image domain to the segmentation network, which generates a segmentation. Using the attenuation network and the recurrent network, the segmentation is iteratively performed. This recurrent application or applications uses the attention network to combine previous segmentations with a reconstructed image or images to generate features used to segment. For example, multi-class attention maps from pre-output segmentations are generated by weighting images based on probability maps of different tissues. The results of the weighting are input to a regularization block of the segmentation network.

Since the machine-learned network was trained with a segmentation loss and not a reconstruction loss, the output segmentation may be more accurate and/or not have to account for noise or artifacts introduced where optimization is performed, at least in part, for the reconstruction.

The segmentation is transmitted over a network, through a communications interface, into memory or database (e.g., to a computerized patient medical record), or to a display. In act 64, the image processor, scanner, or computer generates an image based on the segmentation. The image may be of the segmentation. For example, color coding or shading is used to generate an image showing probability of class membership for one of the classes by spatial location. As another example, the image is of a binary map of spatial distribution, such as by applying a threshold to the probabilities. An image may include a combination of classes. For example, different tissues are shown with different colors.

The image may be an anatomical representation, such as an MR image. The segmentation is used to highlight, mask, or select the anatomy shown in the MR image. In other embodiments, the segmentation is used for further processing to generate the image. For example, the segmentation is used to generate an attenuation map for reconstruction. The reconstruction is performed to generate the image. The displayed image is based on the segmentation due to the use of segmentation in the reconstruction.

The architecture of FIG. 2 may be tested. 20 healthy digital 3D brain volumes are utilized to create the training data. The network is trained on 2D axial slices. 969 slices of 17 brains are used for training, and the remaining 171 slices from 3 brains are reserved for testing. Each digital brain is scanned by a spin echo sequence with Cartesian readout. Average TE=80 ms and TR=3 s are used, and 5% variation of both TE and TR values are introduced for varying MR contrasts in the simulations. All slices have a unified size of 180×216 with 1 mm isotropic resolution. A zero-mean Gaussian distribution with a densely sampled k-space center is used to realize a pseudo-random under-sampling pattern, where 30% phase encoding lines are maintained with 16 center k-space lines. All k-space data are added with additional 10% and 20% white Gaussian noise. All models are implemented in Pytorch and trained on NVIDIA TITAN Xp. Hyperparameters are set as: a learning rate of $10^{-4}$ with decreasing rate of 0.5 for every 20 epochs, 50 maximum epochs, and batch size of 12. The Adam optimizer is used in training all the networks.

Dice's score is use for evaluating performance of output segmentation. For the recurrent steps T, the segmentation performance in terms of Dice's score converges after two iterations or one recurrence. T=2 is set empirically.

The effect of different losses may be tested. Table 1 shows the results. Training and testing using a reconstruction loss ($l_2$) performs the worst, as shown in the first row of Table 1. This verifies that reconstruction from the images with noise and artifacts may compromise segmentation results. The model optimized solely using segmentation loss ($l_{ce}$) on the final segmentation estimation $s_T$ achieves the best result. Due to the efficiency of the attention module, the trained neural network automatically learns image features that benefits the segmentation performance, without constraints on the reconstructed image. Cumbersome tweaking of loss weights between reconstruction and segmentation tasks may be avoided.

TABLE 1

| Loss | 10% noise | | | | 20% noise | | | |
| --- | --- | --- | --- | --- | --- | --- | --- | --- |
| | CSF | GM | WM | Aver. | CSF | GM | WM | Aver. |
| $l_{ce}(s_T) + l_2(x_T)$ | 0.8048 | 0.8841 | 0.8518 | 0.8469 | 0.7995 | 0.8751 | 0.8092 | 0.8279 |
| $\Sigma_{t=0}^{T} l_{ce}(s_t)$ | 0.8513 | 0.9082 | 0.8796 | 0.8797 | 0.8041 | 0.8733 | 0.8283 | 0.8352 |
| $l_{ce}(s_T)$ | 0.8482 | 0.9102 | 0.8814 | 0.8799 | 0.8083 | 0.8762 | 0.8415 | 0.8423 |

The effect of the attention module may be tested. Two different baselines without the attention module are created: one is a two-step model that contains separate reconstruction and segmentation modules, which are trained separately with reconstruction and segmentation losses; and the other is a Joint model, which also contains these two reconstruction and segmentation modules trained together with only segmentation loss on the final output. In order to evaluate the robustness under different settings, performances of Two-step, Joint, and the neural network with the attention module (SERANet) are created with different numbers of reconstruction blocks (e.g., 2, 4, and 7). Two different reconstruction blocks: one using cascading CNN (Type A) and the other using auto-encoder (Type B) are tested. The Dice's score against number of reconstruction blocks shows that with more cascading reconstruction blocks, the segmentation performances of all tested methods improve. SERANet outperforms the others in all settings, showing the benefit of using the attention module.

Figure 6:
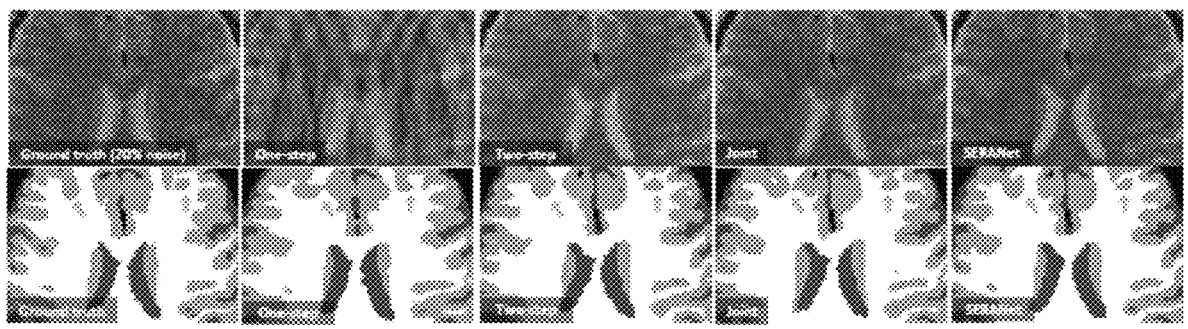
FIG. 6 shows example images and segmentations using different machine-learned networks.

For visualization, a one-step model that takes input as zero-filling images (inverse Fourier transform of under-sampled k-space data) and outputs the segmentation maps is trained. Segmentation results and reconstructed images of models trained by 20% noise data are shown in FIG. 6. SERANet (trained neural network of FIG. 2 using an attention network and recurrent segmentation) predicts more accurate anatomical segmentation details and clearer image contrasts compared to Two-step and Joint. This shows SERANet overcomes the interference with noisy input by using the attention module. In FIG. 6, the segmentation images (bottom row) show CSF, GM and WM parts in each brain as different shades of gray. It can be seen from FIG. 6 that clear boundaries are generated using SERANet with under-sampled k-space data, while the ground truth reconstruction from fully-sampled k-space data contains noise.

SERANet is compared to three state-of-the-art algorithms: LI-net, Syn-net, and Seg-NetMRI. Comparison is also made with the one-step model. Performance of SERANet-7 with 7 reconstruction blocks and SERANet-2 with 2 reconstruction blocks is compared. The results of all methods are shown in Table 2.

example, the server 78 and database 79 are not provided, or only the server 78 and database 79 are provided. In other examples, the server 78 connects through the network 77 with many imaging systems 70 and/or processors 72.

The processor 72, memory 74, and display 76 are part of the medical imaging system 70. Alternatively, the processor 72, memory 74, and display 76 are part of an archival and/or image processing system, such as associated with a medical records database workstation or server, separate from the imaging system 70. In other embodiments, the processor 72, memory 74, and display 76 are a personal computer, such as desktop or laptop, a workstation, or combinations thereof. The processor 72, display 76, and memory 74 may be provided without other components for acquiring data by scanning a patient.

The imaging system 70, processor 72, memory 74 and display 76 are provided at a same location. The location may be a same room, same building, or same facility. These devices are local relative to each other and are remote relative to the server 78. The server 78 is spaced apart by the network 77 by being in a different facility or by being in a different city, county, state, or country. The server 78 and database 79 are remote from the location of the processor 72 and/or imaging system 70. The database 79 may be local to the processor 72.

The imaging system 70 is a medical diagnostic imaging system that uses reconstruction. For example, the imaging system 70 is an MR system. The MR system includes a main field magnet, such as a cryomagnet, and gradient coils. A

TABLE 2

| Method | Pretrain | Loss | 10% noise | | | | 20% noise | | | |
| --- | --- | --- | --- | --- | --- | --- | --- | --- | --- | --- |
| | | | CSF | WM | GM | Aver. | CSF | WM | GM | Aver. |
| One-step | No | $l_{ce}$ | 0.7677 | 0.8334 | 0.7900 | 0.7970 | 0.7600 | 0.8324 | 0.7911 | 0.7945 |
| LI-net [7] | Yes | $l_{ce}$ | 0.6849 | 0.7576 | 0.7558 | 0.7328 | 0.6686 | 0.7276 | 0.7282 | 0.7081 |
| Syn-net [7] | Yes | $l_{ce} + l_2$ | 0.7558 | 0.8256 | 0.7961 | 0.7925 | 0.7307 | 0.8095 | 0.7808 | 0.7737 |
| SegNetMRI [8] | Yes | $l_{ce} + l_2$ | 0.8210 | 0.8905 | 0.8575 | 0.8563 | 0.7817 | 0.8472 | 0.7728 | 0.8006 |
| SERANet-2 | No | $l_{ce}$ | 0.8344 | 0.8977 | 0.8669 | 0.8663 | 0.8053 | 0.8706 | 0.8373 | 0.8377 |
| SERANet-7 | No | $l_{ce}$ | 0.8548 | 0.9175 | 0.8905 | 0.8876 | 0.8122 | 0.8798 | 0.8457 | 0.8459 |

Table 2 shows whether the method is pretrained and what loss the method uses to optimize in columns 2 and 3, respectively. For LI-net and Syn-net, since they perform segmentation from fully-sampled data as a warm start, these approaches are considered as pretraining techniques. SERANet-2 and SERANet-7 consistently outperform the three state-of-the-art approaches for both 10% and 20% noises. Additionally, the Dice's scores drop more for the SegNetMRI when noise level increases compared to SERANet, which may be due to the fact that SegNetMRI contains information from the noisy ground truth images.

Figure 7:
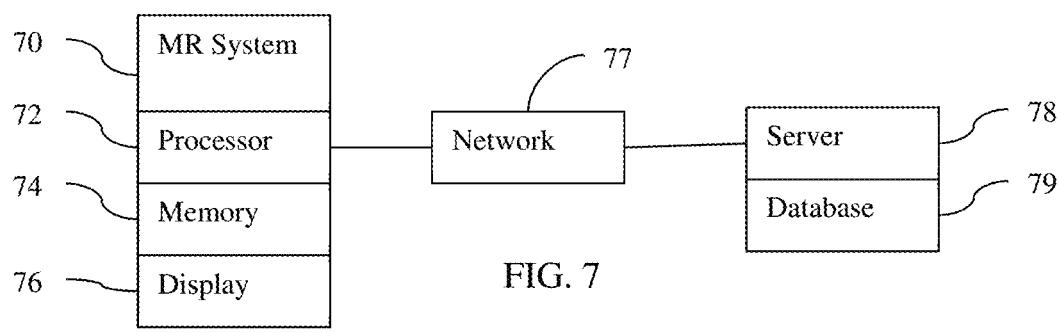
FIG. 7 is a block diagram of one embodiment of a system for machine learning and/or for use of a machine-learned network for segmentation from raw data.

FIG. 7 shows one embodiment of a system for machine learning and/or for application of a machine-learned network. The system is distributed between the imaging system 70 and a remote server 78. In other embodiments, the system is just the server 78 or just the imaging system 70 without the network 77. In yet other embodiments, the system is a computer or workstation.

The system includes an imaging system 70, a processor 72, a memory 74, a display 76, a communications network 77, a server 78, and a database 79. Additional, different, or fewer components may be provided. For example, network connections or interfaces are provided, such as for networking with a medical imaging network or data archival system. In another example, a user interface is provided. As another whole-body coil is provided for transmitting and/or receiving. Local coils may be used, such as for receiving electromagnetic energy emitted by atoms in response to pulses. Other processing components may be provided, such as for planning and generating transmit pulses for the coils based on the sequence and for receiving and processing the received k-space data based on a line order.

The memory 74 may be a graphics processing memory, a video random access memory, a random-access memory, system memory, cache memory, hard drive, optical media, magnetic media, flash drive, buffer, database, combinations thereof, or other now known or later developed memory device for storing data or video information. The memory 74 is part of the imaging system 70, part of a computer associated with the processor 72, part of a database, part of another system, a picture archival memory, or a standalone device.

The memory 74 stores measurements from scan of a patient, such as storing k-space data. An undersampling mask, weights or values of parameters making up some of the layers of the machine-learned network, outputs from different layers or features, one or more machine-learned networks, reconstructed images, segmentation maps, attention maps, and/or images may be stored in the memory 74. The memory 74 may store data during processing for application and/or may store training data and data during processing for machine learning.

The memory 74 or other memory is alternatively or additionally a non-transitory computer readable storage medium storing data representing instructions executable by the programmed processor 72 for training or use of a machine-learned classifier in medical imaging. The instructions for implementing the processes, methods and/or techniques discussed herein are provided on non-transitory computer-readable storage media or memories, such as a cache, buffer, RAM, removable media, hard drive or other computer readable storage media. Non-transitory computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone, or in combination. Likewise, processing strategies may include multiprocessing, multitasking, parallel processing, and the like.

In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

The processor 72 is a general processor, central processing unit, control processor, graphics processor, digital signal processor, three-dimensional rendering processor, image processor, application specific integrated circuit, field programmable gate array, digital circuit, analog circuit, combinations thereof, or other now known or later developed device for machine training or applying a machine-learned network. The processor 72 is a single device or multiple devices operating in serial, parallel, or separately. The processor 72 may be a main processor of a computer, such as a laptop or desktop computer, or may be a processor for handling some tasks in a larger system, such as in the imaging system 70. The processor 72 is configured by instructions, design, hardware, and/or software to perform the acts discussed herein.

The processor 72 is configured to perform the acts discussed above for training or application. For training, the processor 72 or another processor (e.g., the server 78) generates examples by simulating MR scan of digital phantoms. The processor 72 uses machine learning based on the stored and/or created training data and a defined network architecture. For application, the processor 72 uses a stored machine-learned network. Raw data (e.g., k-space measures) of a given patient from the MR system 70, the memory 74, or the database 79 is input to the machine-learned network, which outputs the segmentation for that given patient.

The processor 72 is configured to transmit the segmentation over the network 77, to the display 76, or to the memory 74. The processor 72 may be configured to generate a user interface for requesting and/or presenting the segmentation with or without one or more images reconstructed from the raw data for the patient.

The display 76 is a monitor, LCD, projector, plasma display, CRT, printer, or other now known or later developed devise for outputting visual information. The display 76 receives images, graphics, text, quantities, or other information from the processor 72, memory 74, imaging system 70, and/or server 78. One or more medical images are displayed. The MR images are of a region of the patient, such as a segmented region based on segmentation. The image may include an indication, such as a graphic or colorization, of the classification results, such as the segmentation.

The network 77 is a local area, wide area, enterprise, another network, or combinations thereof. In one embodiment, the network 77 is, at least in part, the Internet. Using TCP/IP communications, the network 77 provides for communication between the processor 72 and the server 78. Any format for communications may be used. In other embodiments, dedicated or direct communication is used.

The server 78 is a processor or group of processors. More than one server 78 may be provided. The server 78 is configured by hardware and/or software. In one embodiment, the server 78 performs machine learning with training data in the database 79. The machine-learned network is provided to the processor 72 for application. The results of classification may be received from the processor 72 for use in further training. Alternatively, the server 78 performs the application on raw data received from the imaging system 70 and provides the segmentation to the imaging system 70.

The database 79 is a memory, such as a bank of memories, for storing training data. Weights or values of parameters of machine-learned network are stored in the database 79 and/or the memory 74.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for segmentation from raw data of a magnetic resonance imager, the method comprising:
    acquiring, by the magnetic resonance imager, k-space data representing response from a patient;
    segmenting an object of the patient represented in the k-space data by a machine-learned neural network, the machine-learned neural network having a segmentation network recurrently applied to output an output segmentation of the object in response to input of the k-space data to the machine-learned neural network; and
    generating an image based on the segmentation.

2. The method of claim 1 wherein acquiring comprises acquiring with undersampling according to an undersampling mask, the machine-learned neural network including a data consistency layer configured to replace k-space lines from a reconstruction image with the k-space data for the k-space lines based on input of an undersampling mask.

3. The method of claim 1 wherein the machine-learned model comprises a sequence of reconstruction blocks and data consistency layers, a last one of the data consistency layers outputting to the segmentation network, wherein segmenting comprises outputting the output segmentation after two or more of the recurrent applications of the segmentation network.

4. The method of claim 1 wherein segmenting comprises segmenting with the machine-learned neural network having been trained with a segmentation loss and not a reconstruction loss.

5. The method of claim 1 wherein segmenting comprises segmenting with the segmentation network, a regularization block, and a data consistency layer being recurrently applied to generate the segmentation.

6. The method of claim 1 wherein segmenting comprises segmenting with the segmentation network recurrently applied two or three times.

7. The method of claim 1 wherein segmenting comprises segmenting with the machine-learned neural network including an attention network, the attention network generating multi-class attention maps from pre-output segmentations by the segmentation network.

8. The method of claim 7 wherein generating comprises generating by weighting images based on probability maps of different tissues as the pre-output segmentations, results of the weighting input to a regularization block of the segmentation network.

9. The method of claim 1 wherein segmenting comprises segmenting with the machine-learned neural network having been trained with training data generated by undersampling outputs of a magnetic resonance simulation from digital phantoms.

10. A method for segmentation from raw data of a magnetic resonance imager, the method comprising:
  acquiring, by the magnetic resonance imager, k-space data representing response from a patient;
  segmenting an object of the patient represented in the k-space data by a machine-learned neural network, the machine-learned neural network including an attention network, the machine-learned neural network outputting an output segmentation of the object in response to input of the k-space data to the machine-learned neural network; and
  generating an image showing the segmentation.

11. The method of claim 10 wherein segmenting comprises segmenting by machine-learned neural network, the machine-learned neural network having a segmentation network recurrently applied to output the output segmentation.

12. The method of claim 10 wherein acquiring comprises acquiring with undersampling according to an undersampling mask, the machine-learned neural network including a data consistency layer configured to replace k-space lines from a reconstruction image with the k-space data for the k-space lines based on input of an undersampling mask.

13. The method of claim 10 wherein the machine-learned model comprises a sequence of reconstruction blocks and data consistency layers, a last one of the data consistency layers outputting to the segmentation network, wherein segmenting comprises segmenting with the machine-learned neural network having been trained with a segmentation loss and not a reconstruction loss.

14. The method of claim 10 wherein segmenting comprises generating, by the attention network, multi-class attention maps from pre-output segmentations by the segmentation network.

15. The method of claim 14 wherein generating comprises generating by weighting images based on probability maps of different tissues as the pre-output segmentations, results of the weighting input to a regularization block of a segmentation network.

16. The method of claim 10 wherein segmenting comprises segmenting with the machine-learned neural network having been trained with training data generated by undersampling outputs of a magnetic resonance simulation from digital phantoms.

17. A method for training segmentation from raw data of a reconstruction medical imager, the method comprising:
  generating training data comprising pre-reconstruction measures and segmentation maps, the training data generated by medical imaging simulation of digital phantoms; storing the trained neural network; and
  defining the neural network to include recurrent segmentation and an attention layer configured to output multi-class segmentation probability maps to a regularization block.

18. The method of claim 17 wherein generating comprises generating k-space or sinogram data as the pre-reconstruction measures, further comprising removing some of the k-space or sinogram data in a simulation of undersampling, and wherein training comprises training based on the training data resulting from the simulation of undersampling.

19. The method of claim 17 wherein training comprises training with a segmentation loss and not a reconstruction loss.

* * * * *